(12) United States Patent
Fischer et al.

(10) Patent No.: US 6,596,874 B1
(45) Date of Patent: Jul. 22, 2003

(54) PROCESS FOR PREPARING AMLODIPINE BENZENESULPHONATE

(75) Inventors: Janos Fischer, Budapest (HU); Katalin Szöke, Budapest (HU); Laszlo Dobay, Budapest (HU); Sandor Leval, Biatorbagy (HU)

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 0 days.

(21) Appl. No.: 10/019,424

(22) PCT Filed: Jul. 5, 1999

(86) PCT No.: PCT/HU99/00050

§ 371 (c)(1),
(2), (4) Date: Dec. 20, 2001

(87) PCT Pub. No.: WO01/02360

PCT Pub. Date: Jan. 11, 2001

(51) Int. Cl.[7] .................. C07D 213/44; A61K 31/4418
(52) U.S. Cl. .................. 546/321; 546/316; 546/321; 546/322; 514/350
(58) Field of Search .................. 514/350; 546/316, 546/321, 322

(56) References Cited

FOREIGN PATENT DOCUMENTS

| EP | 0 089 167 | 9/1983 | |
| EP | 0 244 944 | 11/1987 | |
| EP | 0244944 | * 11/1987 | ......... C07D/211/90 |
| EP | 0 599 220 | 6/1994 | |
| EP | 0599220 | * 6/1994 | ......... C07D/211/90 |
| EP | 0 901 016 | 3/1999 | |

* cited by examiner

*Primary Examiner*—Alan L. Rotman
*Assistant Examiner*—Janet Coppins
(74) *Attorney, Agent, or Firm*—Herbert Dubno; Jonathan Myers

(57) ABSTRACT

The invention relates to a novel process of amalodipine benzenesulphonate of formula (I) by reacting a new 2-[/2-carboxy-benzoyl)-aminoethoxy/methyl/]-4-(2-chlorophenyl)-3-ethoxycarbonyl-5-methoxycarbonyl-6-methyl-1,4-di-hydropyridine derivative of general formula (II) wherein X represents hydrogen or alkali metal or alkali earth metal or quaternary ammonium—with benzenesulphonic acid.

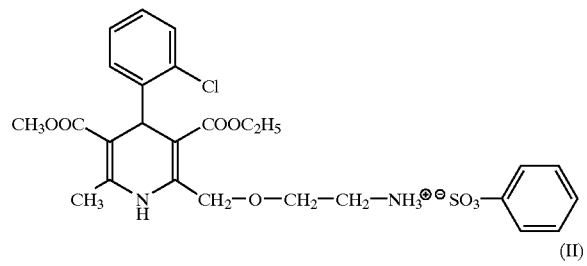

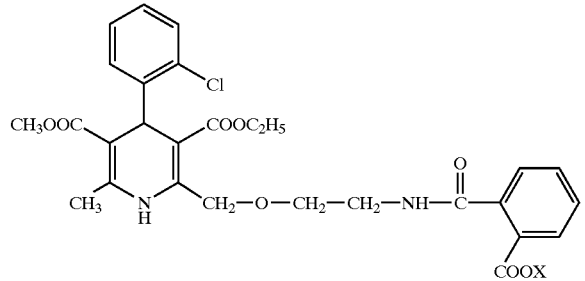

10 Claims, No Drawings

PROCESS FOR PREPARING AMLODIPINE BENZENESULPHONATE

The invention relates to a novel process for preparing amlodipine benzenesulphonate (besylate) of formula (I)

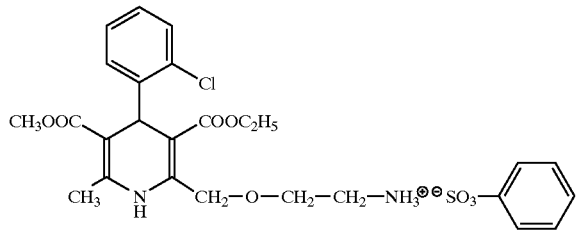

and pharmaceutical preparations containing the same.

According to the process disclosed in the invention the amlodipine benzenesulphonate was prepared by reacting a novel phthalamidic acid {2-[/2-N-(2-carboxy-benzoyl)-aminoethoxy/-methyl]-4-(2-chlorophenyl)-3-ethoxycarbonyl-5-methoxycarbonyl-6-methyl-1,4-dihydropyridine} derivative of general formula (II)

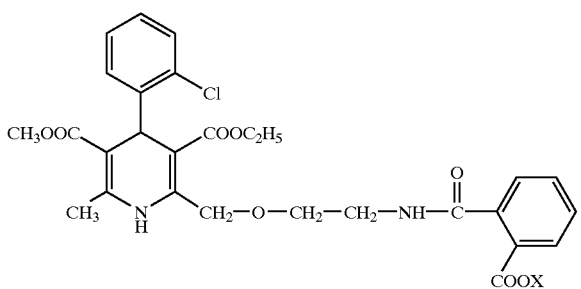

wherein X represents hydrogen or alkali metal or alkali earth metal or quaternary ammonium—with benzenesulphonic acid.

The invention relates also to the novel phthalamidic acid derivatives of general formula II—wherein X represents hydrogen or alkali metal or alkali earth metal or quaternary ammonium—per se and the process for producing the same. These compounds are new final key intermediates (precursors) in the synthesis of amlodipine benzenesulphonate.

The invention relates also to a process for preparing a pharmaceutical composition containing amlodipine benzenesulphonate when prepared according to the process of this invention.

Amlodipine {2-[(2-aminoethoxy)]-methyl-4-(2-chlorophenyl)-3-ethoxycarbonyl-5-methoxycarbonyl-6-methyl-1,4-dihydropyridine} benzenesulphonate is a calcium channel blocking agent of a long duration of action, which is very useful in the treatment of ischaemic heart disease and hypertension.

Amlodipine and the salts thereof were reported first in the European Patent Specification No. 89167 as one of the claimed novel 1,4-dihydropyridines and pharmaceutically acceptable salts thereof. Of the different salts the maleate is disclosed as being particularly preferred.

In the process according to the European Patent Specification No. 89167 1,4-dihydropyridines including amlodipine and the salts thereof are produced from a precursor which can be the corresponding azido derivatives being converted to the amino group by reduction, e.g. with triphenylphosphine or zinc and hydrochloric acid or by hydrogenation over palladium catalyst. The disadvantage of this process is the relatively poor yield of the process for preparing the corresponding azide precursor, moreover the manipulation of azide compounds is less convenient due to the well-known explosiveness of the azidic structures.

Other precursor can be an amino-protected 1,4-dihydropyridine. In these cases the amino 1,4-dihydropyridine including amalodipine can be obtained by removal of the protecting group, then the obtained 1,4-dihydropyridine bases including amlodipine were isolated as an oil, and then were treated with acid.

In the case when the protecting group is benzyl, it is removed by catalytic hydrogenation over palladium catalyst in a solvent such as methanol at room temperature. When the protecting group is 2,2,2-trichloroethoxycarbonyl, it is removed by reduction with zinc in either formic or acetic acid.

In the case when the protecting group is phthaloyl, it can be removed by reaction with a primary amine, such as methylamine. The phthaloyl group can be removed also with hydrazine hydrate at reflux temperature in a solvent, such as ethanol. The phthaloyl group can be removed also with two equivalents of an alkali metal hydroxide, such as potassium hydroxide at room temperature, followed by refluxing the mixture with an excess of hydrochloric acid or sulphuric acid in tetrahydrofuran and water solution.

The disadvantages of the above mentioned processes are in the relatively poor yields of the processes due to the poor yields in the production of the 1,4-dihydropiridine precursors, whose preparation is carried out by Hantzsch's synthesis of asymmetrical 1,4-dihydropyridine esters. Besides each of the processes has technical, safety and environmental problems, too.

Namely, in the case of removing the phthaloyl group from the phthaloyl amlodipine when methylamine is used the yield of the final maleate salt is low (49%) and the use of the harmful methylamine is required. This reagent is irritating to the eyes and to the respiratory organs (see: Merck-Index p 5944, 11. Ed., Merck and Co., Rahway, USA, 1989). When hydrazine hydrate is used the final amlodipine maleate salt was obtained in a yield of 81%, however, the hydrazine is unambiguously carcinogenic (see: D. Beabei, Sicherheit, Handbuch fürdas Labor, p. 136, GIT-Verlag, Darmstadt, 1991). When alkali metal hydroxide and hydrochloric acid is used the finally obtained amlodipine maleate salt was described in a yield of 81%, however, the process can not be reproduced when followed the description of Example 22, Method C.

In the European Patent Specification No. 244 944 amlodipine besylate per se as a new chemical entity and pharmaceutical compositions containing the same were claimed. Both the preparation of amlodipine besylate by reacting amlodipine base and benzenesulphonic acid and that of the pharmaceutical compositions containing the same by mixing the besylate salt of amlodipine with a pharmaceutically acceptable diluent or carrier are also described and claimed, since amlodipine besylate is found to be more advantageous over the previously described salts, e.g. maleate salt, etc. because the previously described salts were not acceptable for pharmaceutical formulation purposes.

The following two methods for the preparation of amlodipine besylate was described in the European Patent Specification No. 244 944.

In the first case amlodipine base was reacted with nearly stoichiometric amount of benzenesulphonic acid in a methanolic suspension and the amlodipine besylate was obtained in a yield of 83.8%. In the second version amlodipine base was reacted with ammonium benzene sulphonate in methanol, then after a short heating under reflux the amlodipine besylate was isolated in a yield of 70%.

In this patent specification the preparation of the starting amlodipine base was not described.

The European Patent Specification No. 599 220 describes a process for the preparation of amalodipine benzenesulphonate by reacting a novel trityl-protected amlodipine base with benzenesulphonic acid in a methanolic or an aqueous methanolic medium at a temperature range from 20° C. to the reflux temperature and then the amlodipine benzenesulphonic acid was isolated and purified.

Although the aim of the above invention was to find a simple and easily feasible way which would afford the desired amlodipine benzenesulphonate in a high yield and high purity without supplementary preparation and isolation of amlodipine in a form of base as it was described in the previously mentioned two European patent specifications, the process disclosed in this patent specification, however, has also some disadvantages. Namely, the starting N-tritylethanolamine was produced in a rather complicated way which is very difficult to apply on industrial scale. Besides the trityl-alkylating may be occurred both on the amino and hydroxy group of the starting ethanolamine, consequently N-trityl, O-trityl and N,O-ditrityl-ethanolamine may be produced simultaneously [see: J. G. Lammer, J. H. van Boom: Recueil Trav. Comm. Pays-Bas, 98(4), 243 (1979)]. Due to the acid lability of the trityl group the Hantzsch reaction can not be accomplished as desired. The duration of the reaction between trityl-protected amlodipine base and benzenesulphonic acid is rather long, i.e. the reaction mixture must be stirred for 13 hours. The product is obtained in a form of resin whereby the processing thereof is extremely complicate including continuous extractions.

It has now unexpectedly been found that amlodipine benzenesulphonate salt can be prepared directly without preparing amlodipine base, contrary to as described in the above European Patents Nos. 89 167 and 244 944, by reacting an easily preparable, new, stable and pure crystalline phthalamidic acid derivative of general formula II—wherein X represents hydrogen or alkali metal or alkali earth metal or quaternary ammonium—with benzenesulphonic acid in a one-step synthesis.

The amount of benzenesulphonic acid is at least a stoichiometric amount or a small excess of benzenesulphonic acid is to be used. The reaction time is 3 to 4 hours.

The new phthalamidic acid derivatives of general formula II—wherein X represents hydrogen or alkali metal or alkali earth metal or quaternary ammonium—can be prepared selectively by reacting 4-(2-chlorophenyl)-3-ethoxycarbonyl-5-methoxycarbonyl-6-methyl-2-(2-phthalimidoethoxy)methyl-1,4-dihydropyridine with a strong base. The thus obtained compound of general formula II—wherein X represents alkali metal or alkali earth metal or quaternary ammonium group—can be isolated or without isolation, if desired, can be reacted with an acid to obtain phthalamidic acid derivative of general formula II, wherein X represents hydrogen.

The starting material of this process can be obtained conventionally by Hantzsch reaction.

Acceptable strong bases can be alkali metal hydroxides, e.g. potassium hydroxide, sodium hydroxide, lithium hydroxide, etc., or alkali earth metal oxides, e.g., calcium oxide, etc., or hydroxides or quaternary ammonium bases, e.g., tetramethylammonium hydroxide, etc.

The quantity of the strong bases is not decisive, however, practically at least a stoichiometric amount of strong base or more conveniently a slight excess of strong base is required.

For the neutralisation step a stoichiometric amount of acid according to the applied base is required.

The reaction with a strong base is carried out at room temperature and the neutralisation step with the acid is carried out during ice-cooling.

The invention is described in more detail as follows.

In the process according to the invention the new phthalamidic acid or its basic salt of general formula II—wherein X represents hydrogen or alkali metal or alkali earth metal or quaternary ammonium—was reacted with at least a stoichiometric amount of the aqueous solution of benzenesulphonic acid under inert atmosphere, conveniently under nitrogen or argon in a mixture of an organic solvent and water, conveniently in a 2:1 mixture of water and acetonitril under heating. The reaction temperature amounts to 70–80° C. and the reaction time is about 3 to 4 hours. The amlodipine benzenesulphonate of the formula I can be obtained in a good yield (80–90%) and in a high purity (>99.5% by HPLC).

The advantages of the process according to the present invention can be summarized as follows.

1. The new phthalamidic acid derivatives which are new key intermediates in the synthesis of amlodipine benzenesulphonate are obtained selectively and in a pure crystalline form. Consequently the amlodipine benzenesulphonate is prepared also in high purity from the new pure crystalline phthalamidic acid derivative.

2. The overall yield of the process for the production of amlodipine benzenesulphonate via the new phthalamidic acid derivatives is much higher than that of the prior art, since the isolation of the amlodipine base is avoided.

3. The whole working procedure of the present invention is essentially shorter and more simple than those described in the prior art.

4. The process of the present invention is easily applicable on industrial scale.

5. The fact that the final intermediates of the process according to the invention are obtained selectively and are isolated in a pure crystalline form is highly favourable for the purposes of the Good Manufacturing Practice which is essential for an active pharmaceutical ingredient.

6. The use of hydrazine or methyl amine, which reagents are harmful to the health and to the environment can be avoided, because no deprotection of the amino group is needed.

The following examples illustrate the process according to the invention without limitation.

EXAMPLE 1

Amlodipine Benzenesulphonate

2-[/2-N-(2-carboxy-benzoyl)-aminoethoxy/methyl]-4-(2-chlorophenyl)-3-ethoxycarbonyl-5-methoxycarbonyl-6-methyl-1,4-dihydropyridine (3.9 g) was suspended in a mixture of water (100 ml) and acetonitrile (60 ml) under argon at room temperature and benzenesulphonic acid (1.2 g ) in a solution of water (20 ml) was added to the suspension. The reaction mixture was stirred at 80° C. for 3 to 4 hours. Then the solvent was evaporated and the product was crystallised by cooling, then filtered and washed with water. The title product (3.5 g; 87%) was obtained, which was recrystallised from a mixture of ethyl acetate and methanol.

Melting point: 200–204° C.; TLC (Kieselgel, Merck 5719), $R_f$: 0.31 (pyridine/acetic acid/water/ethylacetate 16/5/9/70).

EXAMPLE 2

Amlodipine Benzenesulphonate

2-[/2-N-(2-carboxy-benzoyl)-aminoethoxy/methyl]-4-(2-chlorophenyl)-3-ethoxycarbonyl-5-methoxycarbonyl-6- methyl-1,4-dihydropyridine sodium salt (5.8 g) was suspended under argon in a mixture of distilled water (120 ml) and acetonitrile (70 ml), then benzenesulphonic acid (3.5 g) in a solution of distilled water (20 ml) was added to the mixture. The reaction mixture was stirred for 3 to 4 hours at 70–80° C. After evaporation of the solvent the title compound (5.5 g) was crystallised by cooling. The title compound was recrystallised from ethanol to give 4.5 g (80%) of the purified product.

EXAMPLE 3

2-[/2-N-(2-Carboxy-benzoyl)-aminoethoxy/methyl]-4-(2-chlorophenyl)-3-ethoxy-carbonyl-5-methoxycarbonyl-6-methyl-1,4-dihydropyridine (Formula II, wherein X represents hydrogen)

a.) Preparation With Potassium Hydroxide 4-(2-chlorophenyl)-3-ethoxycarbonyl-5-methoxycarbonyl-6-methyl-2-[(2-phthalimido-ethoxy)-methyl]-1,4-dihydropyridine (10.8 g) was suspended in isopropanol (80 ml), then a solution of potassium hydroxide (1.6 g) in water (40 ml) was added to the suspension with stirring at room temperature under nitrogen for 3 to 4 hours. During ice-cooling 1 N hydrochloric acid solution (28 ml) was added and the precipitated product was filtered and washed with water. The title compound (10.9 g, 98%) was obtained, melting point: 167–169° C.

TLC (Kieselgel) $R_f$: 0.29 (benzene/methanol 14/3).

1H NMR CHARACTERIZATION

Instrument: Varian UNITYINOVA 500 (500 MHz for 1H) [D6] DMSO as solvent, TMS as internal standard; (30° C.).

δ: 1.10 t (3H, OCH2CH3); 2.22 s (3H, CH3); 3.43–3.48 m (2H, OCH2-CH2NH); 3.50 s (3H, OCH3); 3.56–3.65 m (2H) (2H, OCH2-CH2NH); 3.92–4.10 m (2H) [OCH2CH3]; 4.58 d (1H) and 4.67 d (1H) [—CH2O—]; 5.31 s (1H) [CH]; 7.11 td (1H), 7.21 td (1H), 7.26 dd (1H), 7.34 dd (1H), 7.42 dd (1H), 7.51 td (1H), 7.57 td (1H), 7.78 dd (1H) [ArH]; 8.41 t (1H) & 8.43 s (1H) [2×NH]; 12.90 br s (1H) [COOH].

b.) Preparation With Sodium Hydroxide 4-(2-chlorophenyl)-3-ethoxycarbonyl-5-methoxycarbonyl-6-methyl-2-[(2-phthalimidoethoxy)-methyl]-1,4-dihydropyridine (6.5 g) was suspended in isopropanol (20 ml) at room temperature under argon, then 1N sodium hydroxide solution was added to the suspension. The reaction mixture was stirred at room temperature for 3 to 4 hours. After evaporation of the isopropanol the residue was cooled in ice and 1N hydrochloric acid solution was added. The obtained title compound (6.4 g, 96%) was obtained, melting point: 165.5–166° C.

c.) Preparation With Lithium Hydroxide 4-(2-chlorophenyl)-3-ethoxycarbonyl-5-methoxycarbonyl-6-methyl-2-[(2-phthalimido-ethoxy)-methyl]-1,4-dihydropyridine (2.7 g) was suspended in isopropanol (20 ml) at room temperature under argon, then a solution of lithium hydroxide (0.4 g) in water (20 ml) was added to the suspension. The reaction mixture was stirred at room temperature for 2 to 3 hours. After evaporation of the isopropanol it was cooled in ice and 1N hydrochloric acid solution was added. The title compound (2.6 g, 93%) was obtained, melting point: 165.5–166° C.

b.) Preparation With Calcium Oxide 4-(2-chlorophenyl)-3-ethoxycarbonyl-5-methoxycarbonyl-6-methyl-2-[(2-phthalimido-ethoxy)-methyl]-1,4-dihydropyridine (3.0 g) was dissolved in a mixture of tetrahydrofuran (30 ml) and water (20 ml) and calcium oxide (0.31 g) was added to the mixture with stirring. The reaction mixture was stirred for 1 hour at room temperature, then it was cooled in ice and 1N hydrochloric acid solution was added. After evaporation of the tetrahydrofuran the crystalline product was filtered and washed with water. The title compound (3.0 g, 97%) was obtained, melting point: 165.5–166° C.

c.) Preparation With Tetramethylammonium Hydroxide 4-(2-chlorophenyl)-3-ethoxycarbonyl-5-methoxycarbonyl-6-methyl-2-[(2-phthalimido-ethoxy)-methyl]-1,4-dihydropyridine (3.0 g) was dissolved in tetrahydrofuran (30 ml) and 25% tetramethylammonium hydroxide (4.0 ml) in water was added to the reaction mixture, which was stirred for 1 hour at room temperature. Then the reaction mixture was acidified with 2N hydrochloric acid solution (6 ml). After evaporation of the tetrahydrofuran in vacuo the residue was crystallised with diethyl ether to afford the title compound (3.0 g; 97%), melting point: 165–166° C.

EXAMPLE 4

2-[12-N-(2-Carboxy-benzoyl)-aminoethoxy/methyl] 4-(2-chlorophenyl)-3-ethoxy-carbonyl-5-methoxycarbonyl-6-methyl-1,4-Dihydropyridine Sodium Salt 4-(2-chlorophenyl)-3-ethoxycarbonyl-5-methoxycarbonyl-6-methyl-2-[(2-phthalimido-ethoxy)-methyl]-1,4-dihydropyridine (6.5 g was suspended in isopropanol (20 ml) at room temperature under argon, then 1N sodium hydroxide solution (20 ml) was added. The reaction mixture was stirred for 3 to 4 hours at room temperature. A clean solution was formed. The solvent was evaporated and the oily residue was crystallised from water, filtered, washed with water to give the title compound (6.9 g), melting point: 140–146° C.

TLC (Kieselgel) Rf: 0.72 (pyridine, acetic acid, water, ethyl acetate 16/5/9/70).

EXAMPLE 5

Formulation of Tablets Containing Amlodipine Benzenesulphonate

Anhydrous calcium hydrogenphoshate (315 g) and microcrystalline cellulose (525 g, 90 µm) are combined and transferred into a drum. Then amlodipine benzenesulphonate (70 g) and microcrystalline cellulose (187.5 g, 50 µm) are combined and passed through a screen into the drum containing the above powder mixture. The screen used in the previous step is rinsed with microcrystalline cellulose (525 g, 90 µm). Anhydrous calcium hydrogenphosphate (315 g) was added to the mixture and the whole mixture was blended for 10 minutes. Then sodium starch glycolate (40 g) was added to the mixture followed by blending for 6 minutes. Finally magnesium stearate (20 g) was added and the resulting mixture was blended for 3 minutes. The powder mixture was then pressed into tablets by conventional methods.

This method was used to make tablets containing different concentrations of the amlodipine benzenesulphonate salt.

What is claimed is:

1. A process for the preparation of a compound of formula (I)

(I)

which comprises the step of reacting a compound of the formula (II)

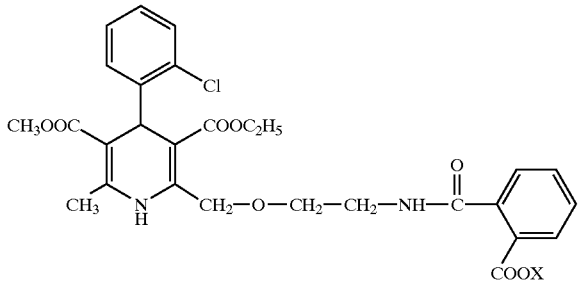

(II)

wherein X is hydrogen or alkali metal or alkaline earth metal or quaternary ammonium—with benzensulphonic acid.

2. A process according to claim 1, characterized in that the compound of the formula II is reacted with at least a stoichiometric amount of benzensulphonic acid.

3. A process according to claim 1, characterized in that the reaction was carried our in an inert solvent at an elevated temperature.

4. A compound of the formula (II)

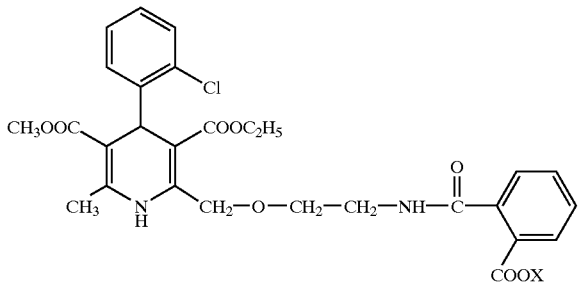

(II)

wherein X is hydrogen or alkali metal or alkaline earth metal or quaternary ammonium.

5. 2-[/2-N-(2-carboxy-benzoyl)-aminoethoxy/methyl]-4-(2-chlorophenyl)-3-ethoxy-carbonyl-5-methoxycarbonyl-6-methyl-1,4-dihydropyridine.

6. Process for the preparation of a compound of formula II—wherein X is hydrogen or alkali metal or alkaline earth metal or quaternary ammonium which comprises the step of reacting 4-(2-chlorophenyl)-3-ethoxycarbonyl-5-methoxycarbonyl-6-methyl-2(2-phthalimidoethoxy)methyl-1,4-dihydropyridine with a strong base, and if desired, reacting the obtained compound of formula II—wherein X is alkali metal or alkaline earth metal or quaternary ammonium—with or without isolation with an acid to obtain the compound of the formula (II) where X is hydrogen.

7. Process according to claim 6, characterized in that the strong base is alkali metal hydroxide, alkaline earth metal oxide or hydroxide, or quaternary ammonium base.

8. Process according to claim 7, characterized in that the strong base is used in at least a stoichiometric amount of the 4-(2-chlorophenyl)-3-ethoxycarbonyl-5-methoxycarbonyl-6-methyl-2(2-phthalimidoethoxy)methyl-1,4-dihydropyridine to obtain the compound of the formula (II) wherein X is alkali metal, alkaline earth metal or ammonium and, if desired, neutralizing said compound of formula (II) with a stoichiometric amount of acid to obtain a compound of the formula (II) wherein X is hydrogen.

9. Process according to claim 7 characterized in that the reaction with the strong base is carried out at room temperature and the reaction with the acid is carried out during ice-cooling.

10. A process according to claim 6 which further comprises the step of reacting the compound of the Formula (II) with benzene sulphonic acid to obtain amlodipine benzenesulphonate.

* * * * *